United States Patent [19]

Abe et al.

[11] 4,297,340

[45] Oct. 27, 1981

[54] COSMETIC COMPOSITION FOR SKIN AND HAIR TREATMENT

[75] Inventors: Yoshiaki Abe, Tokyo; Shigeo Inoue, Ichikai; Atsuo Ishida, Chiba, all of Japan

[73] Assignee: Kao Soap Co., Ltd., Tokyo, Japan

[21] Appl. No.: 75,009

[22] Filed: Sep. 13, 1979

[30] Foreign Application Priority Data

Sep. 26, 1978 [JP] Japan .................... 53/118413

[51] Int. Cl.³ .................. A61K 7/06; A61K 7/08; A61K 7/025; A61K 7/027

[52] U.S. Cl. .................. 424/70; 424/49; 424/63; 424/168; 424/358; 424/365; 536/115; 536/116; 536/119

[58] Field of Search ............... 424/70; 536/116, 119, 536/120

[56] References Cited

U.S. PATENT DOCUMENTS

| | | | |
|---|---|---|---|
| 1,320,855 | 11/1919 | Henderson | 424/DIG. 5 |
| 2,422,633 | 6/1947 | Petersen | 536/119 |
| 2,450,079 | 9/1948 | Brown | 536/116 |
| 2,626,935 | 1/1953 | De Groote | 536/116 |
| 2,908,681 | 10/1959 | Anderson et al. | 536/116 |
| 3,102,114 | 8/1963 | Komori et al. | 536/116 |
| 4,032,702 | 6/1977 | James | 536/115 |

Primary Examiner—Dale R. Ore
Attorney, Agent, or Firm—Oblon, Fisher, Spivak, McClelland & Maier

[57] ABSTRACT

A cosmetic composition comprising as an essential component a glycolipid ester represented by the formula,

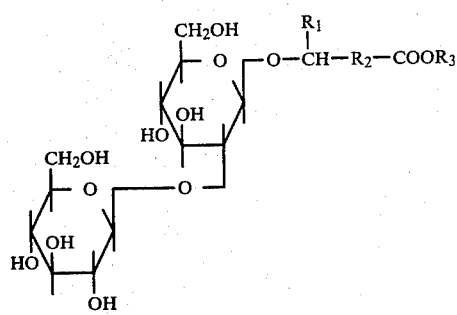

wherein $R_1$ represents a methyl group or a hydrogen atom; $R_2$ represents a saturated or unsaturated hydrocarbon group having 11 to 15 carbon atoms when $R_1$ is a methyl group, or a saturated or unsaturated hydrocarbon group having 12 to 16 carbon atoms when $R_1$ is a hydrocarbon atom; and $R_3$ represents a saturated or unsaturated hydrogen group having 1 to 20 carbon atoms is effective for skin and hair treatment.

3 Claims, No Drawings

COSMETIC COMPOSITION FOR SKIN AND HAIR TREATMENT

BACKGROUND OF THE INVENTION

1. Field of the Invention

This invention relates to cosmetics for use in skin and hair treatment, more particularly to a new cosmetic composition comprising a glycolipid ester as an essential component.

2. Description of the Prior Art

In general, a certain group of substances have been used as a moisturizer in cosmetics of the type described above. Such moisturizer functions to keep the hair from becoming dry or rough and to prevent the moisture against evaporation or escape from inside of the skin so that the hair and skin may be rendered substantially moist and fresh-looking. Known as the moisturizer are polyols such as glycerine, propylene glycol and the like, amino acids and derivatives thereof such as sodium pyrrolidoncarbonate and the like, and oils such as hydrocarbons, higher alcohols, higher fatty acids, esters and the like.

However, when added to a shampoo or rinse which requires washing after its application, the known moisturizer such for example as glycerine of a water-soluble character is almost completely washed away upon washing of the cosmetic and cannot exert any moisture-retaining activity. In contrast, the moisturizer of an oily character makes the cosmetic oily and sticky and hence gives a disagreeable finishing touch to the hair. Glycerine remains deposited excessively on the skin when used in creams in which proper deposition on the skin is essential, while the oily moisturizer has the drawback that it blocks the skin membrane and often results in damaged skin. Therefore, a need continues to exist for moisturizing substances capable of imparting a satisfactory finishing touch to the skin and hair while at the same time eliminating the adverse properties attributable to the known moisturizer.

In view of that situation, the present inventors have made intensive studies on a variety of compounds, and as a result, have found that a particular glycolipid ester acts as an excellent moisturizer which achieves the above desired properties and gives the best results. Based upon this finding, the present invention has been accomplished.

SUMMARY OF THE INVENTION

It is one object of the invention to provide a new cosmetic composition which can overcome the above noted defects of the prior art cosmetics.

It is another object of the invention to provide a new cosmetic composition which comprises a glycolipid ester as an essential component and which can impart a pleasant finishing touch to the skin and hair.

Briefly stated, according to the present invention, there is provided a cosmetic composition comprising as an essential component a glycolipid ester represented by the formula,

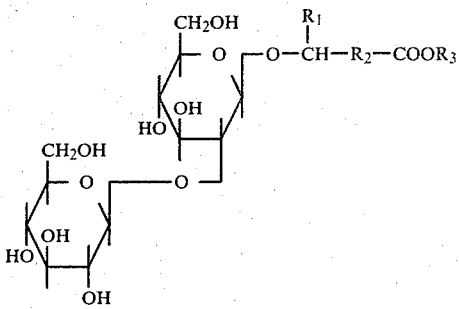

wherein $R_1$ represents a methyl group or a hydrogen atom; $R_2$ represents a saturated or unsaturated hydrocarbon group having 11 to 15 carbon atoms when $R_1$ is a methyl group, or a saturated or unsaturated hydrocarbon group having 12 to 16 carbon atoms when $R_1$ is a hydrogen atom; and $R_3$ represents a saturated or unsaturated hydrocarbon group having 1 to 20 carbon atoms.

DETAILED DESCRIPTION OF THE PREFERRED EMBODIMENTS

A glycolipid ester which is useful in the present invention can be produced by subjecting Sophorolipid which is a fermentation product of Torulopsis bombicola to a methanolysis reaction under acidic conditions by addition of methanol, and subsequently subjecting the resulting methyl ester to an ester exchange reaction in the presence of an alkali catalyst by addition of an alcohol corresponding to the intended ester (Japanese Patent Applications No. 53-17400 and No. 53-17401).

The glycolipid ester thus obtained is a compound which possesses broad HLB characteristics with both a hydrophilic property due to its Sophorose group and a hydrophobic property arising from the hydrocarbon group. Consequently, it should be noted that the HLB values depend on the types and functions of cosmetics actually utilized and can be suitably adjusted by the carbon atom number of the hydrocarbon group represented by $R_3$ in the formula illustrated above.

In the practice of the present invention, the glycolipid ester should have 1 to 20 carbon atoms, preferably 14 to 18 carbon atoms, in $R_3$ in the formula. The properties of various derivatives of the glycolipid ester which are typical of and useful in the invention are listed in Table 1. These properties are based upon Davis' HLB method [Proc. 2nd Inter Congress of Surface Activity, 1426(1957)].

TABLE 1

| Ester derivatives | Surface tensions (dyne/cm$^2$) | HLB values |
| --- | --- | --- |
| Methyl | 40.0 | >20 |
| Ethyl | 39.5 | >20 |
| Propyl | 38.0 | >20 |
| Butyl | — | >20 |
| Hexyl | — | 20 |
| Octyl | — | 17 |
| Decyl | — | 15 |
| Lauryl | — | 13 |
| Mrystyl | — | 10 |
| Palmityl | — | 8 |
| Stearyl | — | 6 |
| Oleyl | — | 7 |

In order to achieve the desired moisture-retaining activity, it is preferred that any selected one derivative of the glycolipid ester be added in amounts of 0.1 to 50% by weight, particularly 1 to 15% by weight of the cosmetic composition. By the term cosmetics used herein are meant all of conventional cosmetics for purposes of skin and hair treatment which include, for instance, various creams, milky lotions, beauty washes, facial packs, hair rinses, hair treatment, shampoos, soaps, lip rouge, foundations, dentifrice and the like.

Other components or additives may be advantageously employed which include, for instance, various oils, surface active agents, alcohols, viscosity modifiers, wetting agents, antiseptics, drugs or chemicals, pigments, perfumes and water.

Suitable oils which are useful in the invention include liquid paraffin, vaseline, paraffin wax, squalane, ceresine wax, bees wax, spermaceti, carnaba wax, hardened castor oil, olive oil, tsubaki oil, lanolin, lanolin alcohol, lanolin fatty acids, higher alcohols, fatty acids, synthetic ester oils of higher alcohols and fatty acids and the like. Suitable surface active agents include polyoxyethylene alkyl ethers, polyoxyethylene fatty acid esters, polyoxyethylene sorbitan fatty acid esters, sorbitan fatty acid esters, glycerine fatty acid esters, polyoxyethylene glycerine fatty acid esters, polyoxyethylene hardened castor oil, polyoxyethylene sorbitol fatty acid esters, polyoxyethylene-polyoxypropylene condensates and the like. Suitable alcohols include ethanol, isopropanol and the like. Suitable viscosity modifiers include carboxylmethyl cellulose, methyl cellulose, hydroxyethyl cellulose, polyvinyl alcohol, polyvinylpyrrolidone, tragacanth gum, carrageenan, locust been gum, dextrin, dextrin fatty acid esters, carboxyvinyl polymer, gelatin, sodium alginate, acacia and the like. Suitable wetting agents include sorbitol, glycerine, propylene glycol, 1,3-butylene glycol, sodium pyrrolidonecarbonate, lactic acid, sodium lactate, polyethylene glycol and the like. Suitable antiseptics include p-hydroxybenzoic acid alkyl esters, sodium benzoate, potassium sorbate, phenoxyethanol and the like. Further, suitable drugs or chemicals include vitamines, antiinflammatory agents and germicides.

Having describes the invention, a further understanding can be obtained by reference to certain specific Examples which are provided for purposes of illustration only and are not intended to be construed as limiting unless otherwise indicated. The Reference Examples are illustrative of the preparation of the glycolipid ester which is useful in the invention.

REFERENCE EXAMPLE 1

(1) To a mixture of 1500 g of glucose, 75 g of a yeast extract and 15 g of urea was added water in an amount sufficient to adjust the whole volume to 15 l, and the resulting mixture was sterilized and utilized as a fermentation liquid. To this fermentation liquid was inoculated Torulopsis bombicola which had been cultured in a culture medium of the same composition as the fermentation liquid at 30° C. for 48 hours. The fermentation was carried out under the following conditions: temperature, 20° C.; stirring, 300 rpm; and aeration, 0.33 VVM. The fermentation was first conducted for 24 hours after the inoculation of the microorganisms, and beef tallow was added in an amount of 150 g and then added in the same amount at intervals of 24 hours. The added beef tallow amounted to 900 g. After the final addition, the fermentation was continued for further 24 hours. The fermentation time totaled 168 hours. The Sophorolipid layer which had precipitated at the bottom of a fermentator was collected by decantation and filtration to give 1300 g of Sophorolipid in the form of a paste having a water content of about 50% at a normal temperature.

(2) 100 g of the thus obtained Sophorolipid together with 2.5 g of polypropylene glycol having an average molecular weight of 200 was placed in a 200 ml round bottom flask equipped with a stirrer and a Liebig condenser. The mixture was evaporated with stirring at 80° C. in an oil bath under a reduced pressure of 250 mmHg to eliminate water. About 2 hours later, the distillation of water was completed, and the water content at this time was found to be less than 1%.

(3) To the thus obtained Sophorolipid-polypropylene glycol solution were added 150 g of methanol and then 2.5 g of sulfuric acid, and the resulting mixture was reacted at 40°±2° C. for 90 minutes. The reaction was regarded as having reached completion when many spots shown by the raw material or Sophorolipid converged on one spot corresponding to a glycolipid methyl ester by thin-layer chromatography on silica gel [developing solvent: chloroform-methanol-acetic acid (75:20:5)].

After the completion of the reaction, the mixture was filtered with filtering paper, followed by neutralization with a given amount of potassium hydroxide. The filtrate was again placed in a round bottom flask equipped with a Liebig condenser, and methanol and methyl acetate which had been formed were removed by distillation to obtain 48 g of a mixture containing 94% of a [(2'-O-$\beta$-D-glucopyranosyl-$\beta$-D-glucopyranosyl)oxy]alkanic acid or alkenic acid methyl ester (hereinafter referred to as "methyl ester") as a brown paste in which polypropylene glycol coexisted. This mixture was purified by column chromatography on silica gel, thereby yielding a pure methyl ester as a white paste.

The infrared absorption spectra of this product indicated a peak at 1740 cm$^{-1}$ due to the ketone group of the ester bond, a broad and strong band at 3380 to 3200 cm$^{-1}$ due to the hydroxy group of the sugar, and a peculiar band at 900 to 750 cm$^{-1}$ due to the glucopyranose ring. The nuclear magnetic resonance spectra of the methyl ester indicated a peak at $\delta 3.6$ due to the O-CH$_3$ in a pyridine solvent, a peak at around $\delta 5.5$ due to the double bond peculiar to the unsaturated fatty acid, a broad band at $\delta 3.5$–5.0 due to the sugar moiety, and a sharp peak at $\delta 1.1$–1.6 due to the strong methylene group. Further, from the oil characterization analyses of the methyl ester, it was found that the product was 0 in acid value, 615 in hydroxy value, 88 in saponification value and 87 in ester value. From these results, the product was ascertained to be of a methyl ester structure.

On the other hand, the product was degraded in a 5 N hydrochloric acid-methanol solution under refluxed conditions to obtain 2 moles of methyl glucoside and 1 mole of a hydroxy fatty acid methyl ester, which were quantitatively analyzed by gas chromatography. From these results, the product was ascertained to be of a methyl ester structure.

REFERENCE EXAMPLE 2

Production of various esters of the [(2'-O-$\beta$-D-glucopyranosyl-$\beta$-D-glucopyranosyl)oxy]alkanic acid and alkenic acid:

To a mixture of the methyl ester-polypropylene glycol obtained in Reference Example 1 was added 1.1 moles of an aliphatic alcohol relative to one mole of the methyl ester, and the resulting mixture was subjected to ester interchange by adding 0.5% by weight of sodium methylate. Methanol formed during the reaction was removed by distillation under normal or reduced pressure to obtain various desired aliphatic alcohol esters.

The preparation methods of some typical derivatives of the glycolipid ester are hereinafter described.

(1) Ethyl ester

To 20 g of the methyl ester-polypropylene glycol obtained in Reference Example 1 was added 20 g of ethanol to obtain a homogeneous solution to which was added 0.1 g of sodium methylate. The ester interchange reaction was conducted at 70° C. while removing by distillation ethanol and methanol which gradually formed during the course of reaction. The mixture was neutralized with a sulfuric acid-ethanol solution and filtered. The filtrate was evaporated to eliminate ethanol to give 19 g of an ethyl ester. The reaction progress was observed by measuring the area ratio of the gas chromatographic peaks of the methyl and ethyl esters obtained on a 3% silicon JXR-chromosolve W column having a particle size of 60–80 mesh under a helium gas stream of 0.6 kg/cm$^2$ at a column oven temperature of 310° C. with a hydrogen flame detector using a trimethylsililated product obtained with a trimethylsililating agent. The reaction was terminated when the methyl ester peak disappeared.

(2) Octyl ester

To 20 g of the methyl ester-polypropylene glycol obtained in Reference Example 1 was added 4.2 g of octyl alcohol, and to the mixture was added 5 g of methanol to obtain a homogeneous solution to which was added 0.1 g of sodium methylate. The greater part of methanol was distilled off at 70° C., and the ester interchange reaction was conducted while removing methanol by distillation with stirring under a reduced pressure of 250 mmHg. The reaction progress was observed by gas chromatography as described above, and the reaction was terminated when the methyl ester peak disappeared. The mixture was neutralized with a fixed amount of citric acid to obtain 24 g of an octyl ester.

(3) Lauryl ester

To 20 g of the methyl ester-polypropylene glycol obtained in Reference Example 1 were added 6.1 g of lauryl alcohol, 5 g of methanol and then 0.1 g of sodium methylate. Thereafter, the same procedure as in process (2) above was repeated to yield 26 g of a lauryl ester.

(4) Oleyl ester

To 20 g of the methyl ester-polypropylene glycol obtained in Reference Example 1 were added 8.9 g of oleyl alcohol, 5 g of methanol and then 0.1 g of sodium methylate. Thereafter, the same procedure as described above for process (2) was repeated to give 29 g of an oleyl ester.

The thus obtained octyl ester, lauryl ester and oleyl ester were purified by column chromatography on silica gel, and the resulting pure products were all white paste substances. The IR spectra and NMR spectra of these products were the same with the exception of the variations in the methyl ester spectra and also in the absorption strength of the methylene groups. The octyl ester was decomposed in a 5 N hydrochloric acid-methanol solution to obtain 2 moles of methyl glycoside, 1 mole of a hydroxyfatty acid methyl ester and 1 mole of octyl alcohol. Under the same conditions, the lauryl ester yielded 2 moles of methyl glycoside, 1 mole of a hydroxyfatty acid methyl ester and 1 mole of lauryl alcohol, and the oleyl ester gave 2 moles of methyl glycoside, 1 mole of a hydroxyfatty acid methyl ester and 1 mole of oleyl alcohol.

These products were further ascertained by their hydroxy values, acid values, saponification vales and ester values obtained by the oil analyses, with the results tabulated in Table 2.

TABLE 2

| Ester derivatives | | Hydroxy values | Acid values | Saponification values | Ester values |
|---|---|---|---|---|---|
| Octyl ester | Calculated | 534.7 | 0 | 76.3 | 76.3 |
|  | Found | 530.2 | 0 | 77.5 | 77.5 |
| Lauryl ester | Calculated | 497.0 | 0 | 71.9 | 71.9 |
|  | Found | 503.2 | 0 | 73.0 | 73.0 |
| Oleyl ester | Calculated | 450.4 | 0 | 64.3 | 64.3 |
|  | Found | 445.0 | 0 | 66.1 | 66.1 |

EXAMPLE 1

In a desiccator was placed 100 mg of each of the glycolipid ester derivatives and comparative compounds. These samples were dried sufficiently and then transferred to another desiccator having a relative humidity of 98%. After a predetermined lapse of time, the weight variations of the samples were observed, with the results tabulated in Table 3.

TABLE 3

| Test esters | | After 24 hrs. | After 72 hrs. |
|---|---|---|---|
| Present compounds | Ethyl | 116 (%) | 145 (%) |
|  | Lauryl | 111 | 133 |
|  | Oleyl | 108 | 129 |
| Comparative compounds | Glycerine | 115 | 140 |
|  | Pure lanolin | 105 | 117 |
|  | Sorbitol | 112 | 127 |

As is clear from these results, the glycolipid ester of the invention possesses a moisture-retaining activity substantially equal to glycerine.

EXAMPLE 2

Sample milky solutions were prepared using the glycolipid ester and comparative compounds and having the formulation indicated below. Each of the samples was coated or applied, respectively, to the skin in an amount of 1 g relative to the area of 36 cm$^2$ of the skin surface and to the hair in an amount of 3 g relative to 20 g of a tress. The finishing touch of each of the tested skin and hair was determined by ten female panelists. The tress was washed moderately with water prior to the determination, but the coated skin was used at it was. The results are shown in Table 4.

| Milky Solution Formulation | |
|---|---|
| Test compound | 10.0 (%) |
| Glycerine monostearate | 4.0 |
| Stearic acid | 2.0 |
| Triethanolamine | 2.0 (%) |
| Sodium laurylsulfate | 0.5 |
| Deionized water | 81.5 |

TABLE 4

| | | Stickiness | | Thickness | | Moistness | |
|---|---|---|---|---|---|---|---|
| Test ester | | H | S | H | S | H | S |
| Present compounds | Ethyl | 1.8 | 2.1 | 3.1 | 3.3 | 3.6 | 3.0 |
|  | Oleyl | 3.3 | 3.5 | 3.0 | 4.0 | 4.2 | 4.3 |
| Comparative compounds | Glycerine | 2.5 | 4.7 | 2.3 | 3.8 | 2.0 | 2.2 |

TABLE 4-continued

| Test ester | Stickiness H | Stickiness S | Thickness H | Thickness S | Moistness H | Moistness S |
|---|---|---|---|---|---|---|
| Pure lanolin | 3.7 | 4.9 | 3.6 | 4.5 | 2.0 | 2.1 |
| Liquid paraffin | 3.6 | 4.6 | 3.8 | 4.7 | 2.1 | 2.3 |

The finishing touch is based on the following evaluation standards. The numerals are expressed as the average values of the ten panelists' scores.

| | |
|---|---|
| Nothing | 1 |
| Lacking | 2 |
| Moderate | 3 |
| Fair | 4 |
| Severe | 5 |

As is clear from these results, the glycolipid ester of the invention becomes moderately thick but less sticky and acts as a moisturizer which can impart a moist finishing touch to the skin and hair.

EXAMPLE 3

Nourishing Cream

Starting Materials

| | |
|---|---|
| (1) Glycolipid ester ($R_1$ = $CH_3$, $R_2$ = $C_{15}H_{30}$, $R_3$ = alkyl group of $C_{18}$ with unsaturated bonding at 9- and 10-position) | 5.0 (%) |
| (2) Liquid paraffin | 7.0 |
| (3) Bees wax | 5.0 |
| (4) Stearic acid | 2.0 |
| (5) Glycerol monostearate | 1.0 |
| (6) Polyoxyethylene sorbitan monooleate | 2.0 |
| (7) Methylparaben | 0.1 |
| (8) Butylparaben | 0.1 |
| (9) Triethanolamine | 0.5 |
| (10) Purified water | balance |
| (11) Perfume | 0.3 |

Preparation (1) to (8) were dissolved at 75° C., to which was added with stirring a mixture of (9) and (10) which had been heated at 70° C., and the resulting mixture was cooled to 40° C. Thereafter, (11) was added to the mixture, and the stirring was terminated 35° C. to obtain a nourishing cream.

EXAMPLE 4

Beauty Wash

Starting Materials

| | |
|---|---|
| (1) Glycolipid ester ($R_1$ = $CH_3$, $R_2$ = $C_{15}H_{30}$, $R_3$ = alkyl group of $C_{18}$ with unsaturated bonding at 9- and 10-position) | 2.0 (%) |
| (2) Ethanol | 15.0 (%) |
| (3) Polyoxyethylene (20) cetyl ether | 2.0 |
| (4) Perfume | 0.2 |
| (5) Pigment | 0.2 |
| (6) Purified water | balance |

Preparation (1) to (6) were homogeneously dissolved with stirring at a normal temperature to obtain a beauty wash.

EXAMPLE 5

Hair Rinse

Starting Materials

| | |
|---|---|
| (1) Glycolipid ester ($R_1$ = $CH_3$, $R_2$ = $C_{15}H_{30}$, $R_3$ = $C_{12}H_{25}$) | 3.0 (%) |
| (2) Distearyldimethylammonium chloride | 3.0 |
| (3) Alkylbenzyldimethylammonium chloride | 1.0 |
| (4) Cetyl alcohol | 3.0 |
| (5) Olive oil | 1.0 |
| (6) Pigment | 0.2 |
| (7) Purified water | balance |
| (8) Perfume | 0.2 |

Preparation

A solution of (6) and (7) which had been heated at 65° C. was mixed with a mixture of (1) to (5) having a temperature of 65° C. The resulting mixture was allowed to cool with stirring up to 40° C. to obtain a hair rinse.

What is claimed is:

1. In a cosmetic composition for the treatment of skin and hair, the improvement comprising the addition, as a moisturizer, of from 0.1 to 50% by weight of the composition of a glycolipid ester represented by the formula,

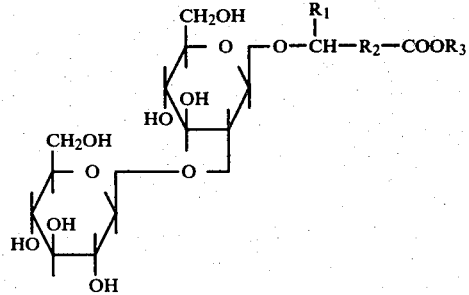

wherein $R_1$ represents a methyl group or a hydrogen atom; $R_2$ represents a saturated or unsaturated hydrocarbon group having 11 to 15 carbon atoms when $R_1$ is a methyl group, or a saturated or unsaturated hydrocarbon group having 12 to 16 carbon atoms when $R_1$ is a hydrogen atom; and $R_3$ represents a saturated or unsaturated hydrocarbon group having 1 to 20 carbon atoms.

2. A cosmetic composition according to claim 1, wherein said glycolipid ester is added in amounts of 1 to 15% by weight of the composition.

3. A cosmetic composition according to claim 1, wherein $R_3$ in the formula has 14 to 18 carbon atoms.

* * * * *